(12) United States Patent
Henschke et al.

(10) Patent No.: US 8,586,729 B2
(45) Date of Patent: Nov. 19, 2013

(54) SYNTHESIS OF DECITABINE

(75) Inventors: Julian Paul Henschke, Harlow (GB); Xiaoheng Zhang, Lianyungang (CN); Jianbo Yu, Tongxiang (CN); Kun Hu, Qitaihe (CN); Lijun Mei, Taihe County (CN)

(73) Assignee: Scinopharm Taiwan Ltd. (TW)

( * ) Notice: Subject to any disclaimer, the term of this patent is extended or adjusted under 35 U.S.C. 154(b) by 294 days.

(21) Appl. No.: 12/572,578

(22) Filed: Oct. 2, 2009

(65) Prior Publication Data

US 2010/0087637 A1 Apr. 8, 2010

Related U.S. Application Data

(60) Provisional application No. 61/102,571, filed on Oct. 3, 2008.

(51) Int. Cl.
C08B 37/00 (2006.01)
C07H 5/04 (2006.01)
C07H 5/06 (2006.01)

(52) U.S. Cl.
USPC ........................................ 536/55.3

(58) Field of Classification Search
None
See application file for complete search history.

(56) References Cited

U.S. PATENT DOCUMENTS 4,209,613 A * 6/1980 Vorbruggen ............... 536/27.11
5,366,987 A 11/1994 Lee et al.
2004/0266996 A1 12/2004 Rabi
2006/0205687 A1 9/2006 Phiasivongsa et al.

FOREIGN PATENT DOCUMENTS

CN 101570559 A 4/2009
EP 2 048 151 A1 4/2009
WO 2009/047313 A2 4/2009

OTHER PUBLICATIONS

Ji et al., Chinese Journal of Pharmaceuticals 2007, 38(7), 468-469.*
Nomura et al., Tetrahedron,2002, 58, 1279-1288.*
Bookser et al., J. Org. Chem., 2007, 72, 173-179.*
Okauchi et al., Chemistry Letters, 1989, 801-804.*
Mikhailov et al., Current Protocols in Nucleic Acid Chemistry, 2006, 1.14.1-1.14.19.*
Niedballa et al., J. Org. Chem. 1974, 39(25), 3672-3674.*
Pearson et al., Journal of the American Chemical Society 1967, 89, 1827-1836.*
Sato et al., Eur. J. Org. Chem., 2002, 87-93.*
Ji, et al, machine translation of Chinese Journal of Pharmaceuticals 2007, 38(7), 468-469, total 4 pages. Translated by Google translator.*
Gomes, et al., Journal of Organometallic Chemistry, 1997, 541, 121-125.*
Evidente et al., Phytochemistry, 1989, 28(10), pp. 2603-2607.*
International Search Report and Written Opinion dated Nov. 11, 2009.
Chen et al., "X-ray structure of 1,3,4-tri-O-acetyl-2-deoxy-β-D-erythro-pentopyranose," Carbohydrate Research, 2009, vol. 344, pp. 2056-2059.
Efange, et al. "Synthesis and Biological Activities of 2-Pyrimidinone Nucleosides. 2. 5-Halo-2-pyrimidinone 2'-Deoxyribonucleosidest" J. Med. Chem. 1985, 28, 904-910.

* cited by examiner

Primary Examiner — Layla Bland
(74) Attorney, Agent, or Firm — Kilpartick Townsend & Stockton LLP

(57) ABSTRACT

A method for producing a β-enriched protected decitabine comprising:
a) coupling a protected 2-deoxy-ribofuranose with a protected 5-azacytosine in the presence of a catalyst to form a reaction mixture comprising the protected decitabine of formula I; and b) quenching the reaction mixture of step a) with a base. The β-enriched protected decitabine so made may be deprotected to produce a decitabine product in a high yield and purity.

22 Claims, No Drawings

SYNTHESIS OF DECITABINE

RELATED APPLICATIONS

The present application claims priority to Provisional Patent Application Ser. No. 61/102,571, filed Oct. 3, 2008, which is incorporated in its entirety by reference.

BACKGROUND OF THE INVENTION

1. Field of the Invention

The present application relates to synthesis of decitabine (also known as 2'-deoxy-5-azacytidine; 5-aza-2'-deoxycytidine; DAC; 5-aza-dC; dezocitidine; and 4-amino-1-(2-deoxy-β-D-erythro-pentofuranosyl)-1,3,5-triazin-2(1H)-one)), which is an active pharmaceutical ingredient (API) useful, among other things, in treating myelodysplastic syndromes (MDS).

2. Description of the Related Arts

A number of methods have been developed to synthesize decitabine but these methods, on the whole, are inefficient and less desirable for commercial production. One important problem is that when the 5-azacytosine ring (s-triazine ring) is conjugated to a carbohydrate, it is sensitive to decomposition by water (under neutral, basic and acidic conditions) and in fact undergoes facile hydrolysis in aqueous formulations, aqueous emulsions, aqueous solutions, and when exposed to moisture during aqueous work-up. This problem makes commercial manufacture of 5-azacytosine based-nucleosides challenging.[1],[2] Another problem in decitabine synthesis is that the key glycosyl donor (carbohydrate ring) and nucleobase coupling reaction that forms the nucleoside itself suffers from poor or a complete lack of anomeric selectivity. Nucleosides and their synthetically produced protected analogues can exist in both α- and β-anomeric forms, but only the β-anomer is usually desired for biological applications. Although the stereochemistry of the anomeric chiral centre is set in the key glycosyl donor and nucleobase coupling reaction, the inventors discovered that under certain conditions that can be used in the manufacture of decitabine, the chiral centre can epimerize (isomerise).

See, e.g., the following references:

(1) J. A. Beisler, *J. Med. Chem.*, 1978, 21, 204.
(2) L. D. Kissinger and N. L. Stemm, *J. Chromatography*, 1986, 353, 309-318.
(3) a) U.S. Pat. No. 3,350,388 (1967) and DE1922702 (1969), Šorm and Pískala (Ceskosl Ovenska Akademieved) and A. Pískala and F. Šorm, Nucl. Acid Chem., 1978, 1, 444-449.; b) A. Pískala and F. Šorm, *Collect. Czech. Chem. Commun.* 1964, 29, 2060.
(4) M. W. Winkley and R. K. Robins, *J. Org. Chem.*, 1970, 35, 491.
(5) Nucleic acids in chemistry and biology, Michael Blackburn, Michael Gait, David Loakes and David Williams (eds), Cambridge, UK. The Royal Society of Chemistry, 2006, Chapter 3, pp 84-85.
(6) J. Ben-Hatter and J. Jiricny, *J. Org. Chem.*, 1986, 51, 3211-3213.
(7) DE2012888 (1971), Vorbrüggen and Niedballa (Schering AG).
(8) U. Niedballa and H. Vorbrüggen, *J. Org. Chem.*, 1974, 39, 3672-3674.
(9) G. Gauberta, C. Mathe', J.-L. Imbacha, S. Erikssonb, S. Vincenzettic, D. Salvatoric, A. Vitac, G. Maurya, *Eur. J. Med. Chem.*, 2000, 35 1011-1019.
(10) U.S. Pat. No. 4,082,911 (1978), Vorbrüggen (Schering Aktiengesellschaft).
(11) CN101307084A (2008) J. R. Fan et. al.

The entire content of each of the above references is incorporated herein as reference.

Pískala and Šorm[3a] teach a lengthy method for the synthesis of decitabine which involves the use of reactive N-glycosylisocyanate intermediates possessing 1-β-configuration. The synthetic process (Scheme 1) comprises reacting a peracyiglycosyl isocyanate with an S-alkylisothiurea to obtain a peracyiglycosylisothiourea, condensing the latter with an orthoester of an aliphatic acid at high temperature (135° C.) to obtain hydroxy-protected glycosyl-4-alkylmercapto-2-oxo-1,2-dihydro-1,3,5-triazine followed by deprotection with sodium methoxide (NaOMe) in methanol (MeOH) followed by decationization using an ion-exchange resin. The intermediate is then aminated with ammonia ($NH_3$) in MeOH in a sealed vessel overnight. Although based on the isocyanate, the overall yield of decitabine is about 30%, it could be difficult to store the isocyanate and its use might provide a health risk. This isocyanate itself is produced from a chlorosugar precursor by reaction with silver cyanate.[3b] The route also suffers from other difficult to scale-up steps, including the use of the carcinogenic ICH Class I solvent benzene, and the need for a pressure vessel in the deprotection step.

Scheme 1 - Isocyanate method for the synthesis of decitabine

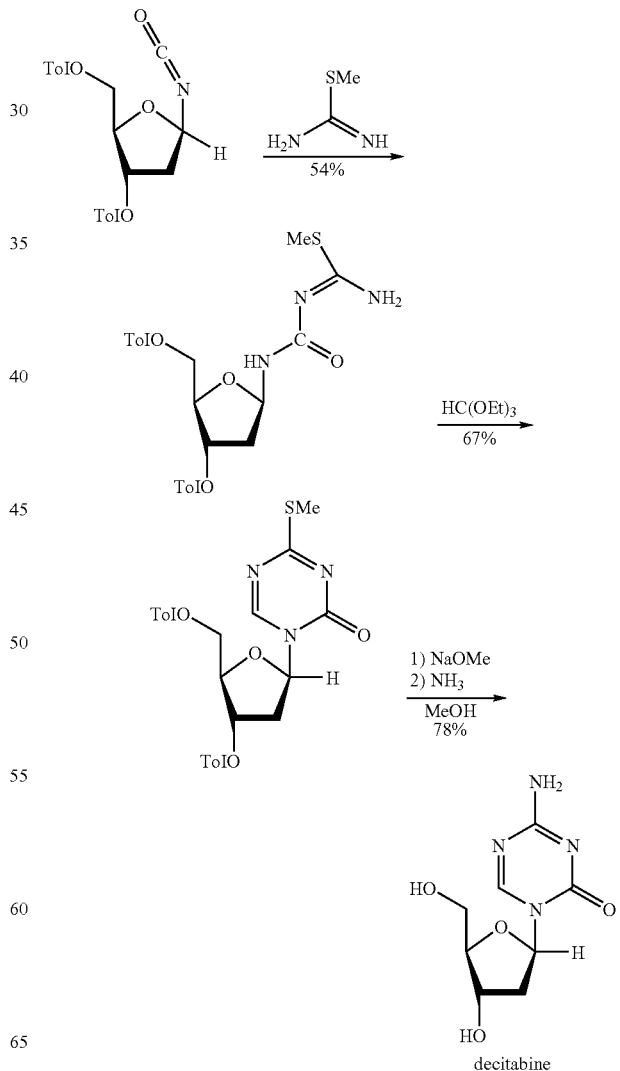

Another potential process for decitabine synthesis was reported by Winkley and Robins[4] (Scheme 2). Their approach utilizes the non-catalysed coupling of a 1-chlorosugar with 2-[(trimethylsilyl)amino]-4-[(trimethylsilyl)oxy]-s-triazine (silyl 5-azacytosine) which probably proceeds via an $S_N2$ mechanism. The yield of the desired β-anomer was very low (7% overall yield) and the process required gaseous hydrogen chloride in the synthesis of the 1-chlorosugar, long reaction times (4-5 days), the need for pressure vessels, complicated column chromatography and lengthy work-up and isolation procedures. Also, 1-halosugars (halogenoses) are not stable. There is no indication that any anomeric selectivity is obtained in this process.

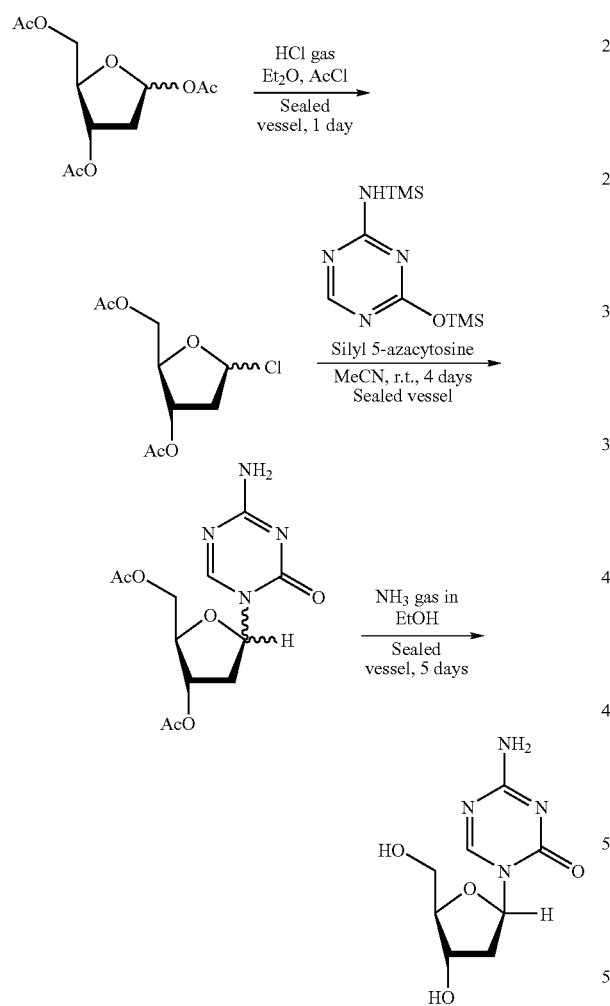

Scheme 2 - Use of a 1-chlorosugars in the synthesis of decitabine

Niedballa and Vorbrüggen[7,8] teach the synthesis of protected (blocked) nucleosides including decitabine that utilizes tin chloride in dichloroethane (DCE) to accelerate the coupling reaction of silyl 5-azacytosine and a protected 1-chlorosugar (Scheme 3). Even though the authors used an anomerically-enriched chlorosugar (α-anomer), an anomeric mixture of protected decitabine isomers was formed. This process suffers from difficulties in removal of tin from the API and emulsions during the aqueous work-up of the coupling mixture. Therefore, this process may not be suitable for the commercial manufacture of decitabine. Due to the sensitivity of the 5-azacytosine ring to water, any process that suffers from the formation of emulsions may potentially provide lower yields and purities of the product due to hydrolysis.

Ben-Hatter and Jiricny[6] also utilise a 1-chlorosugar in a tin chloride catalysed coupling reaction in DCE. To avoid difficulties with the hydrolysis of the sensitive 5-azacytosine ring, the authors instead used Fmoc hydroxy protection groups since these may be removed under non-aqueous, mildly basic conditions. The coupling reaction produced a 1:0.9 mixture, following silica gel chromatography, of the undesired α-anomer and the desired β-anomer of the Fmoc protected decitabine, with the latter in 21% yield based on the 1-chlorosugar (Scheme 3). A drawback of this process is that not only is the protected decitabine isolated as a mixture of anomers, but also the crude decitabine is required fractional crystallization to obtain the desired anomer.

Scheme 3 - Synthesis of protected decitabine using Vorbrüggen's SnCl$_4$ accelerated coupling approach

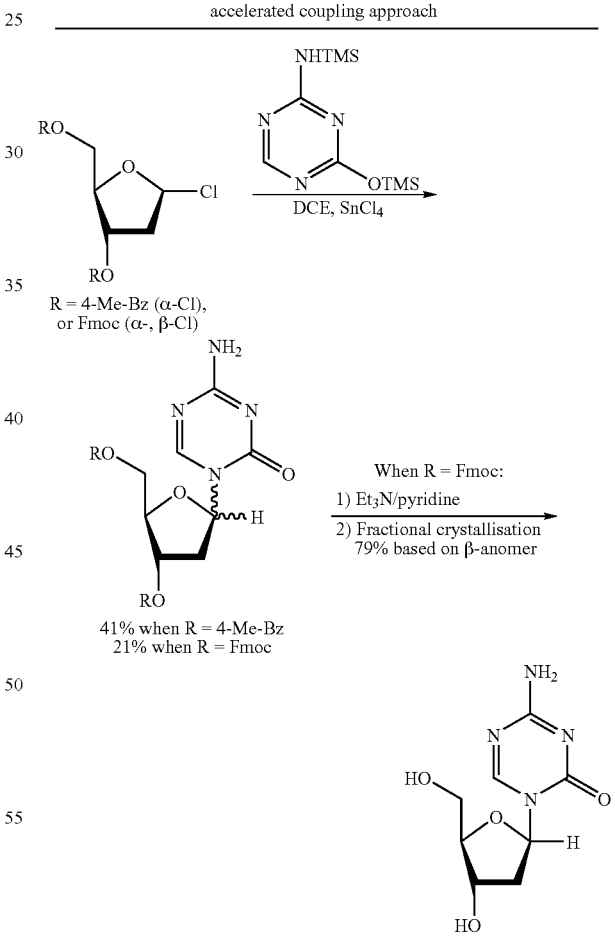

Vorbrüggen[10] teaches a general method for the coupling of silylated heterocyclic organic bases (including cytosine, pyridines triazoles, and pyrimidines, but not 5-azacytosine) with protected 1-O-acyl, 1-O-alkyl or 1-halo-sugars (viz., ribose, deoxyribose, arabinose and glucose derivatives) in benzene, DCE or MeCN to make protected nucleosides (Scheme 4). Decitabine is not specifically described in Vorbrüggen. The coupling is promoted by trimethylsilyl (TMS) esters of esterifiable mineral acids or strong sulfonic acids, including trimethylsilyl triflate (TMSOTf), TMSOClO$_3$ and TMSOSO$_2$F. The use of these silyl ester catalysts in place of tin chloride is an advance in this type of chemistry, because it means that APIs may potentially be manufactured free of tin residues.

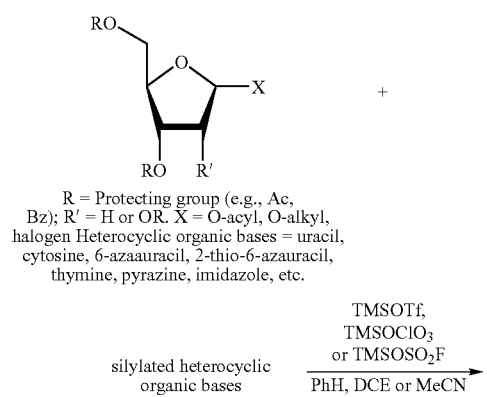

Scheme 4 - Vorbrüggen's coupling protocol utilizing trimethylsilyl esters of strong acids R = Protecting group (e.g., Ac, Bz); R' = H or OR. X = O-acyl, O-alkyl, halogen Heterocyclic organic bases = uracil, cytosine, 6-azauracil, 2-thio-6-azauracil, thymine, pyrazine, imidazole, etc.

-continued

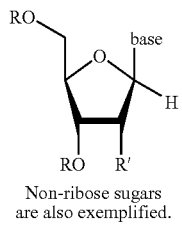

Non-ribose sugars are also exemplified.

As shown above, controlling the stereochemistry of the C1 (anomeric centre) during the synthesis of 2-deoxy-ribose based nucleosides is a challenge.[5] Maury et al.[9] attempt to use a deoxygenation approach, following the direct coupling of silyl 5-azacytosine with a tetraacyl protected ribofuranose sugar, to synthesize the enantiomer of decitabine (ent-decitabine). See Scheme 5 below. Specifically, Maury et al synthesize non-2-deoxy-ribose nucleosides (i.e., synthesis of ribose based nucleosides) followed by deoxygenation of the C2' position. In this way, the synthesis of ent-decitabine proceeds via the related nucleoside ent-azacitidine. The drawback of this approach is that the very expensive Markiewicz reagent (1,3-dichloro-1,1,3,3-tetraisopropyl disiloxane) and tris(trimethylsilyl)silane are used in the deoxygenation part of the synthesis. Column chromatography was also used in most of the steps. The use of expensive silicon-based reagents and the extra synthetic steps required beyond those of a typical nucleoside synthesis make this approach less attractive on a manufacturing scale.

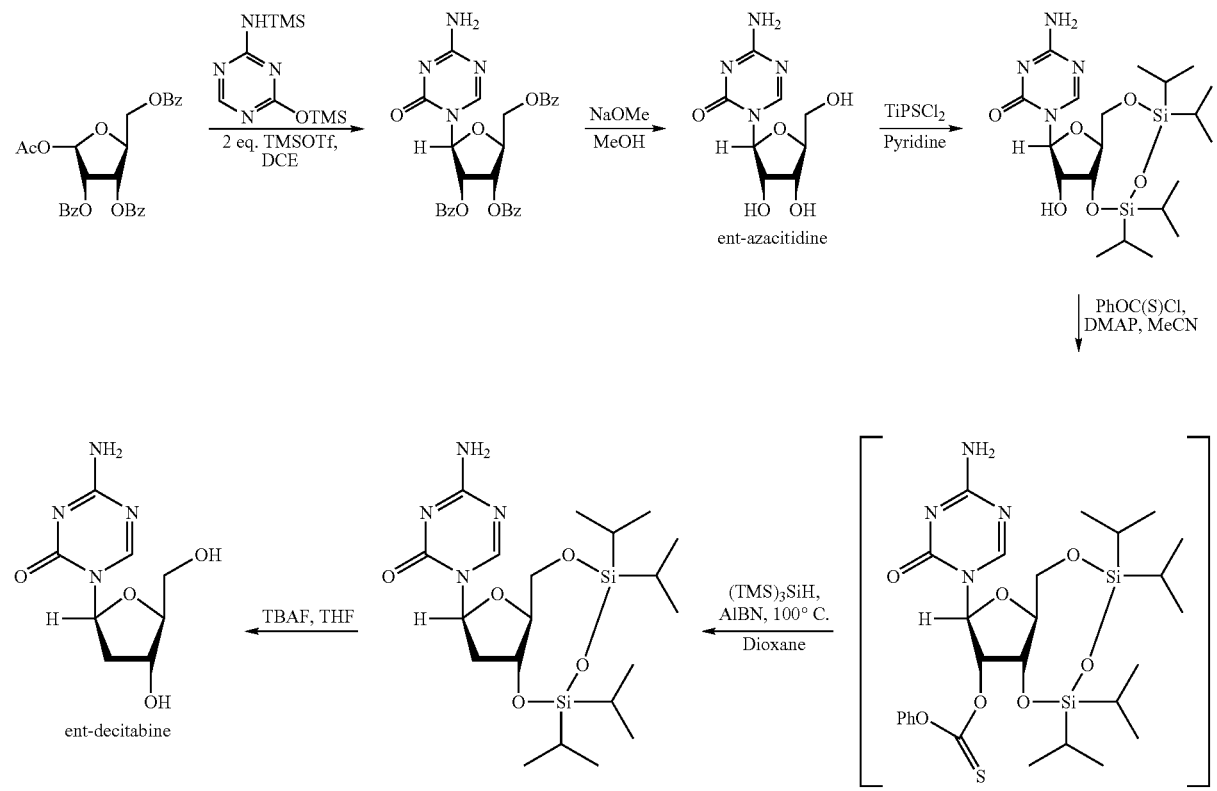

Scheme 5 -Deoxygenation approach to the enantiomer of decitabine (ent-decitabine)

Fan et al.[11] coupled silyl 5-azacytosine and 1-O-acetyl-3,5-di-O-(2-methoxyacetyl)-2-deoxy-D-ribofuranose in toluene at 30-35° C. in the presence of a greater than stoichiometric amount of TMSOTf to provide a protected decitabine as a mixture of anomers (Scheme 6) in only 28% yield. The protected decitabine was deprotection using sodium ethoxide to give decitabine in a low 22% based on the protected decitabine, and a very low 6% overall yield.

Scheme 6 - Fan et. al.'s synthesis of decitabine

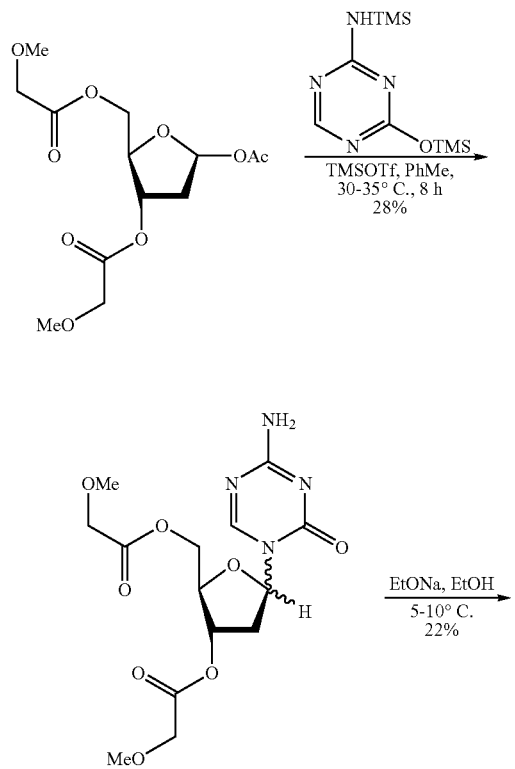

Therefore, there is still a need for a simpler and less expensive process for producing a decitabine on a manufacture scale in a high yield and purity.

SUMMARY OF THE INVENTION

In accordance with one aspect of the present application, a method for producing a β-enriched protected decitabine of formula I:

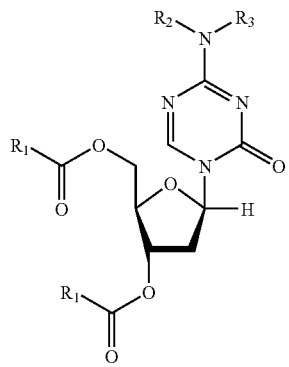

wherein each of $R_1$ is $C_1$-$C_8$ alkyl group or aryl group, each of $R_2$ and $R_3$ is independently hydrogen or $Si(R_4)_3$, and $R_4$ is independently optionally substituted $C_1$-$C_8$ alkyl group or aryl group, comprises:

a) coupling a protected 2-deoxy-ribofuranose of formula II:

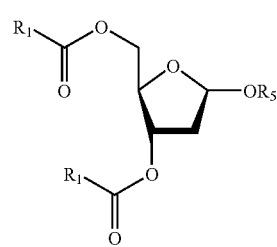

wherein each of $R_1$ is as defined above, and $R_5$ is alkylcarbonyl group, arylcarbonyl group, alkylsulfonyl group, fluoroalkylsulfonyl group or arylsulfonyl group that allows $OR_5$ to behave as a leaving group, with a protected 5-azacytosine of formula III:

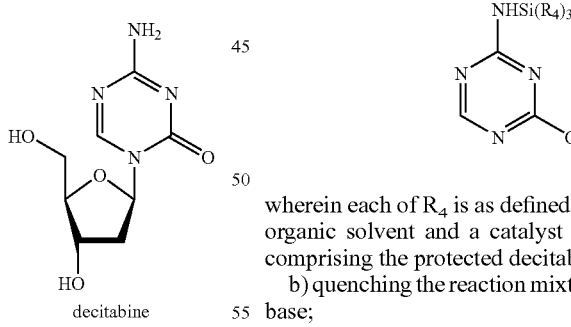

wherein each of $R_4$ is as defined above, in the presence of an organic solvent and a catalyst to form a reaction mixture comprising the protected decitabine of formula I; and b) quenching the reaction mixture of step a) with an organic base;
wherein the organic base is soluble in the organic solvent.

The coupling reaction is conducted preferably at a temperature of 20° C. to −60° C., more preferably, at about 0° C.

The catalyst is preferably a non-metallic Lewis acid or sulfonic acid. The non-metallic Lewis acid is preferably a trialkylsilyl ester of a sulfonic acid. The trialkylsilyl ester of a sulfonic acid is preferably trimethylsilyltrifluoromethylsulfonate (TMSOTf). The sulfonic acid is preferably triflic acid (TfOH).

The organic base preferably an amine, and more preferably a primary amine. The primary amine is preferably $MeNH_2$ or $EtNH_2$.

The organic solvent is preferably dichloromethane, dichloroethane, chloroform, chlorobenzene, acetonitrile or a mixture thereof.

Preferably, as an embodiment of the present application, the protected decitabine is a compound of formula Ia:

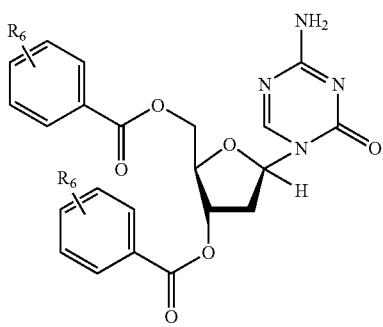

Ia wherein R₆ is hydrogen, alkyl, alkoxy or halide.

Preferably and alternatively, the protected decitabine is a compound of formula Ib:

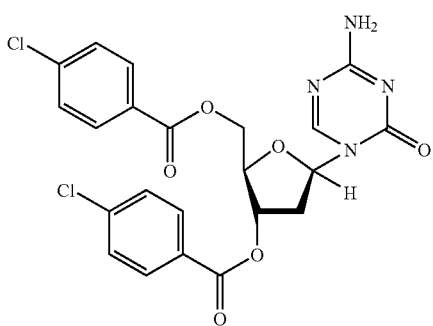

Ib

In accordance with another aspect of the present application, the protected β-enriched decitabine made in accordance with the process as described above may be further deprotected to produce the final API product decitabine:

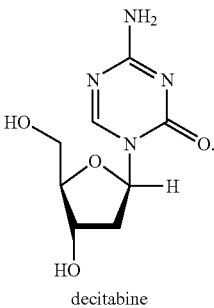

decitabine

As a preferred embodiment, the method may comprise isolating that includes diluting the quenched reaction mixture with a water immiscible organic solvent, washing the organic phase with a basic aqueous solution, separating the organic phase from the aqueous solution, drying the organic phase to remove water; evaporating the organic solvent to obtain the dry and solid protected decitabine and optionally milling the protected decitabine.

The step of deprotecting may be conducted in the presence of a nucleophillic deprotecting agent, such as an alkoxide, ammonia or an amine in an alcohol solvent or in an alcohol/co-solvent mixture. The alkoxide is preferably sodium methoxide.

As an embodiment of the present application, the process may comprise a further step of washing the β-enriched decitabine with an organic solvent. Preferably, the organic solvent is methanol.

As an embodiment of the present application, the process may comprise a step of recrystallizing the β-enriched decitabine in an alcohol solution or an alcohol and dimethylsulfoxide (DMSO) mixture. The alcohol is preferably methanol.

Compared to the methods reported by others, the process described in the present application has the following advantages: 1) the protected precursor intermediate and the final decitabine API product produced in accordance with the process of the present application is free of heavy metal residues; 2) the protected decitabine intermediate produced in accordance with the process of the present application is enriched in the requisite β-anomer, with a smaller relative amount of the undesired α-anomer; and deprotecting the enriched β-anomer of protected decitabine leads to the final decitabine API product in an increased yield; by contrast, prior synthetic methods disclosed in the literature produce protected decitabine intermediates as typically approximately 1:1 mixtures of the α- and β-anomers; 3) the process in accordance with the present application may be conducted economically on a manufacturing scale for the production of human grade API and does not require chromatographic purification in any of the synthetic steps; a single recrystallization step may be optionally used.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

The following describes preferred embodiments of the present invention and should not be used to limit the scope of the present invention.

As used herein, enriched β-enriched protected or enriched β-decitabine means that the ratio of β-anomer and α-anomer is greater than 1:1; preferably the ratio of these two anomers is greater than 2:1, more preferably greater than 2.5:1.

The inventors discovered that the ratio of the undesired α-anomer and the desired β-anomers of the protected decitabine precursor is dynamic both under the reaction conditions the anomers formed and also during the work-up process, specifically due to epimerisation of the carbohydrate C1 chiral centre formed in the coupling reaction. Moreover, the undesired α-anomer was found to become enriched following its formation by this epimerisation. The α-anomer was the thermodynamically favored isomer, and therefore the inventors had to devise a method by which to avoid this, to maintain the relative and absolute amounts of β-anomer initially formed in the coupling reaction.

As stated above, the coupling reaction provides the desired β-anomer compound I along with the undesired α-anomer compound IV:

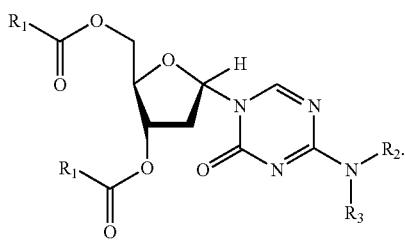

IV

Following work-up, $R_2$ and $R_3$ are both hydrogen.

One aspect of the invention is the quench of the coupling reaction mixture with an organic base. After the coupling reaction and base quench, the reaction may then be diluted with a water immiscible organic solvent and the mixture warms up to ambient temperature. The reaction mixture may then be washed with a basic aqueous solution and the organic phase is dried to remove water.

As noted above, the process for the preparation of protected decitabine compound of formula I:

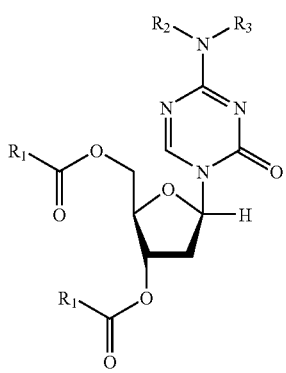

I comprises: coupling a protected 2-deoxy-ribose of formula II:

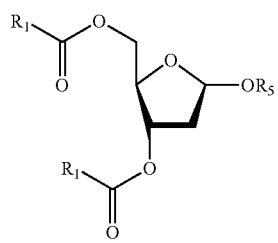

II with a protected 5-azacytosine of formula III:

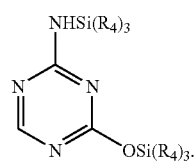

III

Preferably $R_4$ is methyl and $R_5$ is acetyl. In a preferred embodiment the protected decitabine isolated after work-up is the compound of formula Ia:

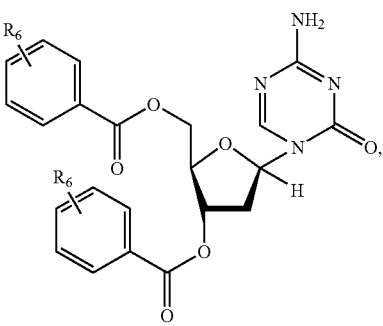

Ia wherein the $R_6$ is hydrogen, alkyl, alkoxy or halide.

It is further preferred that the protected decitabine is the compound of formula Ib.

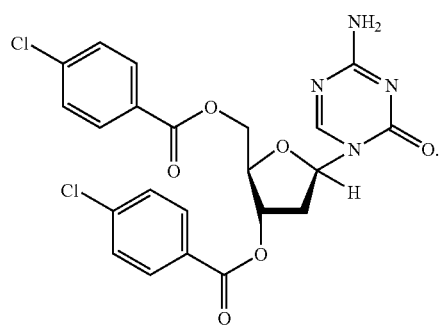

Ib

Before quenching, a trimethylsilyl group might be attached to the free pendant amino group.

$R_5$ is preferably acetyl. Therefore, as a preferred embodiment, the protected decitabine is formed by the coupling of IIIa (2-[(trimethylsilyl)amino]-4-[(trimethylsilyl)oxy]-s-triazine):

IIIa with compound IIa:

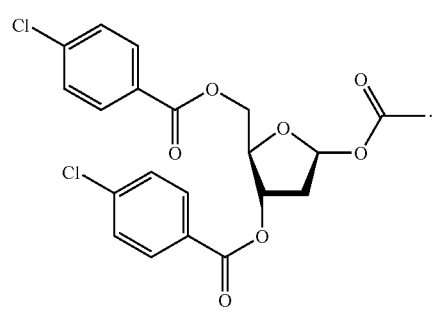

IIa

The coupling reaction provides the desired β-anomer compound Ib along with the undesired α-anomer compound IVa.

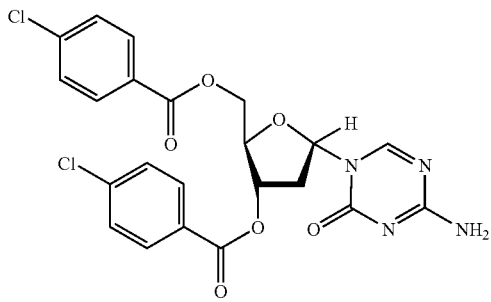

IVa

The inventors discovered that the ratio of the undesired α-anomer IV and the desired β-anomer I is highly variable depending on the coupling conditions and the work-up conditions that are used. A lack of selectivity in the coupling reaction of bases with protected 2-deoxy-ribofuranose compounds is well documented in the literature, but what is not well documented for decitabine synthesis are protocols which can be used to produce the β-anomer protected nucleoside, such as compound I, in a significantly or substantially enriched amount relative to the α-anomer. In fact during their research, the inventors found that the ratio of the undesired α-anomer IVa and the desired β-anomer Ib varied from 1:0.6 to 1:2.6 depending on the choice of solvent, reaction temperature, equivalents of compound IIa with respect to compound IIIa, reaction concentration, and how the reaction work-up was conducted. For example, whereas under very similar reaction conditions the use of dichloromethane (DCM) as a solvent led to good anomeric selectivity (α-anomer IVa and β-anomer Ib ratio was 1:2.6 when the reaction temperature was approximately minus 40° C.), the use of tetrahydrofuran (THF) and toluene as solvents led to poor selectivities (α-anomer IVa and β-anomer Ib ratio was 1:0.6-0.9 when the reaction temperature was approximately minus 40° C.) with decreased purities of the β-anomer Ib (25-35 area % by HPLC as compared to >50 area % when DCM was used as the solvent). When the coupling of compound IIa with compound IIIa was conducted in DCM at about 20° C. the α-anomer IVa and β-anomer Ib ratio was 1:1.3. In fact, when the coupling of compound IIa and IIIa was conducted in DCM with 1 equivalent of TMSOTf, a relationship between reaction temperature and anomeric selectivity was observed. At minus 40° C. the α-anomer IVa and β-anomer Ib ratio was 1:2.6, at minus 15° C. it was 1:1.9, at 2° C. it was 1:1.7 and at 20° C. it was 1:1.3. Most preferably, the coupling reaction was conducted in dry DCM using a trialkylsilyl sulfonic acid ester such as TMSOTf as catalyst at a temperature of less than 20° C. Other silyl ester based catalysts such a TBSOTf can also be used. The preferred temperature is between −40° C. and 5° C. and a 1:1 molar mixture of compound II and compound III are reacted with a slight excess (1.05 equivalents) of TMSOTf. When excess compound III was used with respect to compound II the selectivity for the β-anomer was reduced. More dilute conditions favour an increased amount of the β-anomer with respect to the α-anomer, however, too high dilution (such as 30 volumes of solvent to 1 weight of compound II) is less preferred on a manufacturing scale. Thus it is preferred on a manufacturing scale that approximately 15 volume of DCM to 1 weight of compound IIa is used.

Among various conditions, the inventors unexpectedly found the benefit of quenching the coupling reaction mixture with an organic base in producing a higher ratio of β-anomer and α-anomer. The inventors discovered that if the reaction mixture was allowed to remain unquenched, the ratio of the undesired α-anomer and the desired β-anomers increased with an absolute increase in the amount of α-anomer and an absolute decrease in the amount of β-anomer. That is, without the intent of being bound by any theory, the inventors believe that the ratio change was primarily due to the isomerization of the desired β-anomer into the undesired α-anomer, and was not significantly due to decomposition of the β-anomer.

It was unexpectedly discovered that, if the coupling reaction mixture is left unquenched beyond completion of the coupling reaction, then the amount of β-anomer steadily decreases and that of the α-anomer increases. The rate of isomerization is increased at a higher temperature. The inventors discovered that the rate of isomerization was substantial enough to lead a significant loss of the β-anomer while the work-up has no prior reaction quench even on a sub-kilogram scale. This discovery was not obvious or expected and the inventors' observation of this matter, and the addition of base to quench the reaction, allowed them to develop a process in which more β-anomer can be obtained than otherwise.

Preferably the organic base used for quenching is an organic amine. More preferably, the organic amine is a primary amine, such as MeNH$_2$ or EtNH$_2$. This base quench step is conducted before the standard aqueous base quench step. The amount of the organic amine should be about 1 molar equivalent with respect to 2-deoxy-ribofuranose of formula II. A larger excess of the organic amine base may promote decomposition of the product compound I.

By using an organic soluble base, the quench can be done at a low temperature immediately after the reaction. By contrast quenching with an aqueous bases, such as NaHCO$_3$, requires a warmer temperature to stop ice formation from the aqueous NaHCO$_3$. In addition, the inventors found that quenching the coupling reaction with aqueous NaHCO$_3$, the product mixture had to be pre-diluted with DCM to stop precipitation.

The base is added shortly after the completion of the coupling reaction of 2-deoxy-ribofuranose of formula II and the protected 5-azacytosine of formula III at a temperature that is similar to the temperature at which that the reaction is conducted. If the reaction is allowed to warm up before the organic amine base quenches, the amount of β-anomer compound I is decreased and the amount of α-anomer compound IV is increased. Therefore, the base is added to the coupling reaction mixture preferably within 30 minutes, more preferably within 5 minutes, in particular immediately after the completion of the coupling reaction. The rate of addition should preferably be metered so that an exotherm, which may lead to heating of the reaction mixture and therefore cause significant isomerization, is not generated. The base is preferably added to the coupling reaction mixture when the temperature of the reaction mixture is not more than 20° C., more preferably about 0° C.

In accordance with one embodiment of the present application, the coupling reaction, when conducted under the preferred reaction conditions, provides a product mixture composing an α-anomer to β-anomer molar ratio of 1.0:1.5 or higher such as 1.0:2.0 or even 1.0:2.7, but this depends on the reaction temperature used. Lower coupling reaction temperatures favor higher ratios. More importantly, the temperature in the coupling reaction used should provide not only a good ratio of α-anomer and β-anomers, but in particular a HPLC purity of the β-anomers of about 50% or higher as well as considerations of convenience and short unit operation times in the manufacturing plant. With this goal, a maximum reaction temperature of about 0° C. is preferred along with the DCM soluble base quench immediately following completion of the coupling reaction. This may provide up to about a 40% isolated yield of β-anomer compound Ib on about a 3 Kg manufacturing scale as based on compound IIa. One advantage of obtaining enriched β-anomer compound I is that the subsequent deprotection step proceeds in a higher yield to produce decitabine, as calculated based on the β-anomer. Moreover, the crude decitabine that is isolated is more enriched in the β-anomer when the formerly protected decitabine that was deprotected was more β-anomer enriched. On the laboratory scale, when a 1:3 mixture of the α-anomer and β-anomer protected decitabine was deprotected, a 1:105 mixture of the α-anomer and β-anomers of crude decitabine was isolated. When a 1:1.8 mixture of the α-anomer and β-anomers of protected decitabine was deprotected, a 1:59 mixture of the α-anomer and β-anomers of crude decitabine was isolated. When the protected mixture was 1:1.3, the deprotected mixture was 1:44, and when the protected mixture was 1:1, the deprotected mixture was of the α-anomer and β-anomers of crude decitabine 1:18.

After the coupling reaction and amine base quench, the reaction may then be diluted with a water immiscible organic solvent, preferably DCM, and the mixture warms up to ambient temperature, preferably 25° C. The reaction mixture is then washed with aqueous NaHCO$_3$ solution and the organic phase is dried to remove water to prevent hydrolysis of the protected decitabine dissolved in the organic phase. As noted earlier, the protected decitabine and decitabine are water sensitive.

The inventors unexpectedly discovered that the quality, physical property and water content of the isolated solid compound I was particularly pertinent to the subsequent deprotection step of compound I to decitabine. In fact it was difficult to develop a protocol under which this deprotection step functioned smoothly and consistently. Such difficulties (including hydrolysis) encountered during the deprotection of aroyl protecting groups from compound I using NaOMe in MeOH lead Ben-Hatter and Jiricny[12] to publish an process for decitabine synthesis that utilizes an Fmoc rather than aroyl protecting group for protection of the hydroxy groups (i.e., Ben-Hatter and Jiricny seem to conclude that in decitabine synthesis, it was hard to deprotect aroyl protecting groups (where in compound 1, R$_1$=aryl) due to hydrolysis). Also, the low 22% yield reported by Fan et al.[11] in the deprotection of their protected decitabine might conceivably be due to them not having identified the best conditions and quality of the protected decitabine.

In accordance with one embodiment of the present application, the aqueous NaHCO$_3$ extraction is preferably performed over long enough period so that the silicon residues from the silylated nucleobase and/or the TMSOTf catalyst reagent residues are decomposed by the aqueous base. Otherwise unidentified silicon-based residues may interfere in the subsequent deprotection step and have a retarding influence. The solid compound I is preferably further dried following its isolation to avoid decomposition in the subsequent step. This drying may result in a higher yield of decitabine.

The solid compound I is optionally milled into a fine and consistent powder and dried before the subsequent step. The nature of the solid compound I closely relates to the smooth completion of the subsequent step.

In a further embodiment, the inventors discovered deprotection of the protected decitabine to furnish crude decitabine proceeds smoothly by using dry, solid protected decitabine. The quality, dryness, and physical nature of the solid protected decitabine closely relates to the subsequent deprotection step, because it can be conducted under heterogeneous conditions and basic conditions. When protected decitabine with a ratio of at least 1:1.5 of α-anomer and β-anomers was deprotected on a manufacturing scale, the deprotection step conveniently provides crude decitabine mostly devoid (<1% with respect to the β-anomer as judged by HPLC analysis) of the undesired α-anomer by a simple filtration step.

The deprotection of protected decitabine is a heterogeneous reaction in a mixture of a solid phrase comprising the synthesized decitabine and a liquid phase comprising mostly an organic solvent, such as MeOH. Some, but not all, of the protected decitabine probably is dissolved in the liquid phase. In other words, the reaction is conducted in slurry. Once the deprotection is complete, the heterogeneous mixture that is composed of a solid phase and a liquid phase is simply filtered. No special extra processing steps are required to separate the undesired α-anomer, that has been formed in the prior coupling step, from the β-anomer, because the α-anomer isomer of decitabine remained dissolved in the liquid phase. The collected solid is mostly crude β-enriched decitabine (its HPLC purity is quite high—perhaps typically 96%). The filtrate (i.e., the "liquid phase") contains the organic solvent and the "undesired α-anomer" (i.e., α-decitabine), and probably also decomposed materials, some protected decitabine, and some deprotection intermediates. API grade decitabine may readily be obtained from the crude decitabine produced in the process of the present application by crystallization with HPLC purity ≥99.7% with a quality equal to that of the decitabine commercial brand product.

In another embodiment of the process, a mixture of compounds of the formulae I and IV

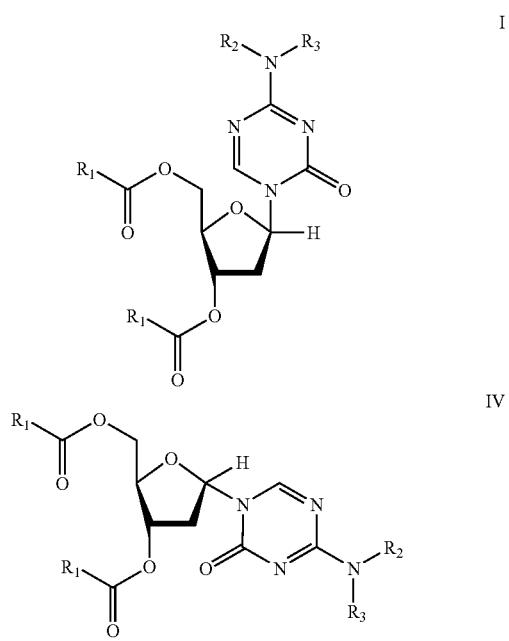

are deprotected using a nucleophilic deprotecting agent to furnish crude decitabine. Deprotection of protected decitabine compound I may be achieved using a nucleophilic deprotecting agent, such as an alkoxide, ammonia or an amine in an alcohol solvent or in an alcohol/co-solvent mixture. Alkoxides include NaOMe. Amines include MeNH$_2$. NaOMe is the preferred deprotection agent. It is preferred that the deprotection step is conducted under heterogeneous conditions. This relies on good quality protected decitabine being used, such as when the material is dry and when the solid is of a homogeneous consistency.

The crude decitabine is simply isolated from the deprotection step substantially devoid (e.g., less than 1 molar % with respect to the β-anomer as judged by HPLC analysis) of its undesired α-anomer V by filtration.

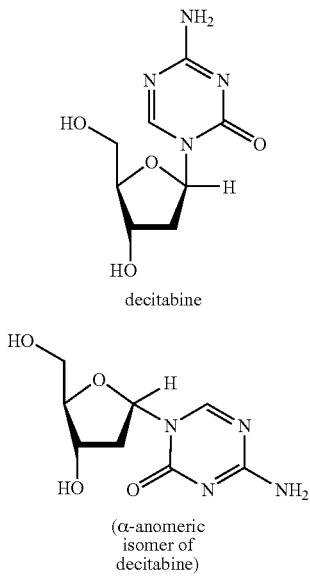

decitabine V (α-anomeric isomer of decitabine)

When 1.7-2.4:1.0 mixtures of compounds Ib and IVa were deprotected on a manufacturing scale, the amount of α-anomer V in the crude decitabine was less than 1 molar % with respect to decitabine as judged by HPLC analysis. Thus, no separate purification step was required to remove the α-anomer V from decitabine, which is an advantage of this invention.

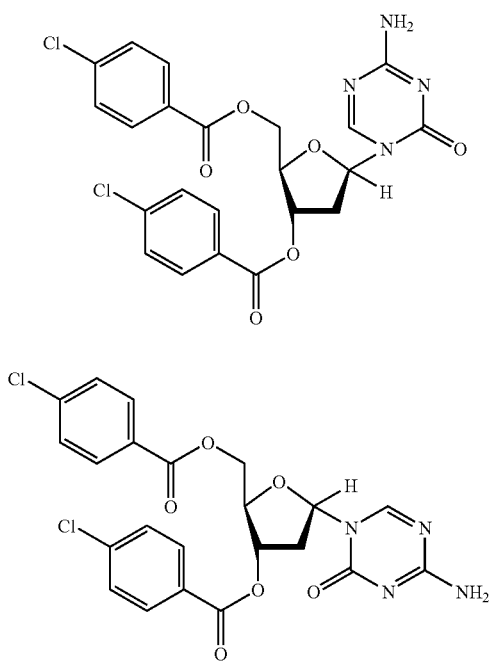

Ib

IVa

When NaOMe is used as the deprotecting agent, an alcohol is the preferred solvent. Solvents that may be used include MeOH and isopropanol. Mixtures of alcohols and DMSO may also be used. The most preferred solvent system is MeOH without a co-solvent because the reaction is heterogeneous and the crude decitabine produced is suspended as a filterable solid in the product mixture, whereas the undesired anomer V is present substantially dissolved in the liquid phase, and therefore the crude decitabine is very conveniently isolated by filtration and then washed with an alcohol, preferably MeOH, and then dried. Deprotection of the Ib and IVa mixture on a 5.5 to 6 Kg manufacturing scale provides a 58 to 66% yield of crude decitabine that has a typical HPLC purity of more than 96%.

In another embodiment of the present application, the crude decitabine is recrystallized from an alcohol solvent or alcohol solvent mixture or an alcohol and co-solvent mixture to give API grade decitabine. Alcohols used include MeOH and isopropanol and other co-solvents include DMSO. When crude decitabine is crystallized from MeOH, high 99.7 to 99.9% HPLC purity decitabine can be recovered in about 65% yield (based on crude decitabine) on a kilogram manufacturing scale.

EXAMPLES

The following examples are provided for the purpose of further illustration only and are not intended to be limitations on the disclosed invention Example 1

Coupling of silyl 5-azacytosine (IIIa) with Protected 2-deoxy-D-ribofuranose (IIa) to Give Protected Decitabine (Ib+IVa)

1-O-Acetyl-3,5-di-O-(4-chloro-benzoyl)-2-deoxy-D-ribofuranose (3.603 Kg, 7.68 mol), 2-[(trimethylsilyl)amino]-4-[(trimethylsilyl)oxy]-s-triazine (1.970 Kg, 7.68 mol) and dichloromethane (71.6 Kg) were charged to a suitable reactor. The mixture was cooled to 0° C. TMSOTf (1.791 Kg, 8.06 mol) was added to the solution at 0° C. and stirred for 5 hours. 2M methyl amine in methanol solution (about 3.95 Kg) was then added to the mixture at 0° C. and stirred for 45 mins. The mixture was diluted with dichloromethane (71.6 Kg) and washed with saturated sodium bicarbonate solution (39.8 Kg) at 25° C. The organic layer was dried using molecule sieves (36 Kg). The molecule sieves were filtered and rinsed with dichloromethane (60.1 Kg). The organic layer was evaporated to dryness at 35° C. The solid was milled and vacuum dried at 45° C. to obtain 2.99 Kg (5.92 mol) of 4-amino-1-[3,5-di-O-(4-chloro-benzoyl)-2-deoxy-β-D-ribofuranosyl]-1H-[1,3,5]triazin-2-one (compound Ib) in 52% HPLC purity (40% yield based on 1-O-acetyl-3,5-di-O-(4-chloro-benzoyl)-2-deoxy-D-ribofuranose) and 4-amino-1-[3,5-di-O-(4-chloro-benzoyl)-2-deoxy-α-D-ribofuranosyl]-1H-[1,3,5]triazin-2-one (compound IVa) mixture in 27% HPLC purity. That α-anomer to β-anomer ratio was 1.0:1.91.

Example 2

Deprotection of Protected Decitabine (Ib+IVa) to Give Crude Decitabine

A mixture of 4-amino-1-[3,5-di-O-(4-chloro-benzoyl)-2-deoxy-β-D-ribofuranosyl]-1H-[1,3,5]triazin-2-one in about 50% HPLC purity and 4-amino-1-[3,5-di-O-(4-chloro-benzoyl)-2-deoxy-α-D-ribofuranosyl]-1H-[1,3,5]triazin-2-one (6.15 Kg, 12.17 mol) and methanol (21.4 Kg) were charged into a suitable reactor at about 25° C. 30% Sodium methoxide in methanol solution (0.61 Kg) was added to the mixture solution and then stirred for 5 hours. The solids were filtered, washed with methanol (3.3 Kg) and dried at 50° C. for 14 hours to obtain 0.927 Kg (4.11 mol) crude decitabine in 97.1% HPLC purity (about 67% yield based on 4-amino-1-[3,5-di-O-(4-chloro-benzoyl)-2-deoxy-β-D-ribofuranosyl]-1H-[1,3,5]triazin-2-one (compound Ib)).

Example 3

Purification of Crude Decitabine

Crude decitabine (1.200 Kg, 5.25 mol) and methanol (86 Kg) were charged to a suitable reactor. The mixture was heated to reflux to completely dissolve the crude decitabine. Activated carbon (24 g) was added to the mixture solution at 64° C. and stirred for 1 hour. The mixture was filtered at 64° C. followed by rinsing with methanol (24 Kg). The filtrate was then distilled at 63° C. to suitable volume (90 L). The solution was cooled down to the cloudy point (56° C.) and held for 1 hour at that temperature. The slurry was then cooled to 5° C. and stirred for 4 hours. The solids were filtered, washed with methanol (2.8 Kg) and dried at 50° C. to furnish 0.75 Kg (3.28 mol) decitabine in 99.7% HPLC purity (65% yield based on crude decitabine).

Example 4

Purification of Crude Decitabine

Crude decitabine (1.5 g) was heated at reflux in anhydrous MeOH (29 mL) for 30 minutes. DMSO (9.3 mL) was added slowly to the solution resulting in almost complete dissolution at 60~65° C. The mixture was filtered, and the filtrate was slowly cooled. At 4° C. the slurry was filtered and the filtered cake was washed three times with MeOH (3 mL each) and dried in vacuo at 50° C. to give 99.82% HPLC pure decitabine (0.9 g).

Example 5

Coupling of silyl 5-azacytosine (IIIa) with protected 2-deoxy-D-ribofuranose (IIa) to give protected decitabine (Ib+IVa)

A mixture of 1-O-acetyl-3,5-di-O-(4-chloro-benzoyl)-2-deoxy-D-ribofuranose (5 g, 90% HPLC pure, equivalent to 9.9 mmol), DCM (50 mL) and 2-[(trimethylsilyl)amino]-4-[(trimethylsilyl)oxy]-s-triazine (2.5 g, 9.9 mmol) was cooled to about 0° C. and TfOH (1.1 g, 6.9 mmol) was added to the solution. The solution is stirred for 5 h at about 0° C. and then diluted with DCM (100 mL) followed by the addition of a saturated aqueous solution of $NaHCO_3$ (75 mL) at 20~25° C. The organic phase was separated, dried over anhydrous $MgSO_4$ and filtered. The $MgSO_4$ was washed with DCM (30 mL) and the filtrates were combined and evaporated to dryness at 20~40° C. under reduced pressure to give 4.5 g of a mixture of 4-amino-1-[3,5-di-O-(4-chloro-benzoyl)-2-deoxy-β-D-ribofuranosyl]-1H-[1,3,5]triazin-2-one (compound Ib) in 37.4% HPLC purity and 4-amino-1-[3,5-di-O-(4-chloro-benzoyl)-2-deoxy-α-D-ribofuranosyl]-1H-[1,3,5]triazin-2-one (compound IVa) in 29.0% HPLC purity.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. It is intended, therefore, that the invention be defined by the scope of the claims which follow and that such claims be interpreted as broadly as is reasonable.

We claim:

1. A method for producing a β-enriched protected decitabine of formula I:

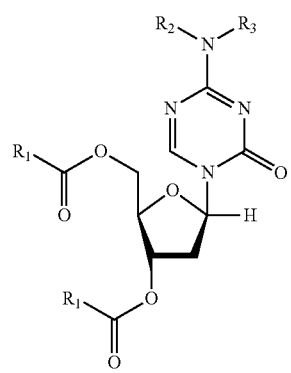

wherein each of $R_1$ is $C_1$-$C_8$ alkyl group or aryl group, each of $R_2$ and $R_3$ is independently hydrogen or $Si(R_4)_3$, and $R_4$ is independently optionally substituted $C_1$-$C_8$ alkyl group or aryl group, comprising:

a) coupling a protected 2-deoxy-ribofuranose of formula II:

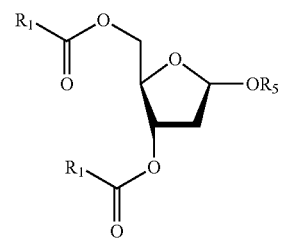

wherein each of $R_1$ is as defined above, and $R_5$ is alkylcarbonyl group, arylcarbonyl group, alkylsulfonyl group, fluoroalkylsulfonyl group or arylsulfonyl group, with a protected 5-azacytosine, of formula III:

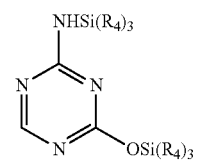

wherein each of $R_4$ is as defined above, in the presence of an organic solvent and a catalyst to form a reaction mixture comprising the protected decitabine of formula I; and b) quenching the reaction mixture of step a) with a primary amine to maintain the ratio of β-anomer to α-anomer of the protected decitabine of formula I in the reaction mixture at no less than 1.5:1;
wherein the primary amine is soluble in the organic solvent.

2. The method of claim 1 wherein the catalyst is a non-metallic Lewis acid or sulfonic acid.

3. The method of claim 1 wherein the organic solvent is selected from the group consisting of dichloromethane, dichloroethane, chloroform, chlorobenzene, and combinations thereof.

4. The method of claim 1 wherein the protected decitabine is a compound of formula Ia:

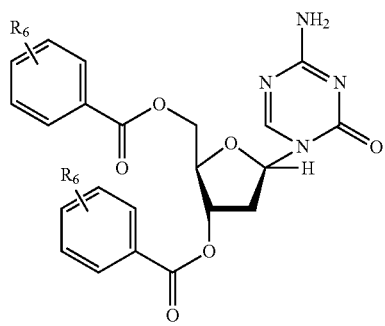

Ia wherein $R_6$ is hydrogen, alkyl, alkoxy or halide.

5. The compound of claim 4 wherein the protected decitabine is a compound of formula Ib:

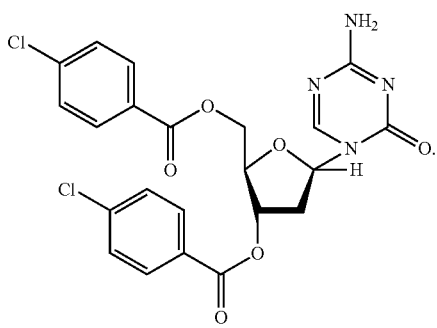

Ib

6. A method for producing a β-enriched decitabine:

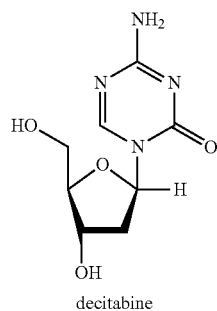 [SMILES: Nc1ncn([C@H]2C[C@@H](O)[C@@H](CO)O2)c(=O)n1]

decitabine comprising:
a) coupling a protected 2-deoxy-ribofuranose of formula II:

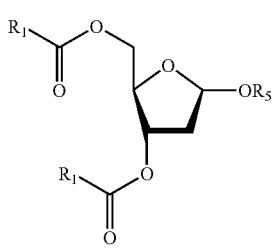

II wherein each of $R_1$ is as defined above, $R_5$ is alkylcarbonyl, arylcarbonyl, alkylsulfonyl, fluoroalkylsulfonyl or arylsulfonyl group, with a protected 5-azacytosine, of formula III:

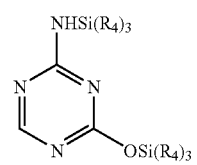

III wherein each of $R_4$ is as defined above, in the presence of an organic solvent and a catalyst to form a reaction mixture comprising protected decitabine;
b) quenching the reaction mixture with a primary amine to maintain the ratio of β-anomer to α-anomer of the protected decitabine in the reaction mixture at no less than 1.5:1, wherein the primary amine is soluble in the organic solvent; and
c) deprotecting the protected decitabine to obtain the β-enriched decitabine.

7. The method of claim 6 comprising a further step of isolating a dry and solid protected decitabine subsequent to the step b) and prior to the step c).

8. The method of claim 7 wherein the step of isolating comprises: 1) diluting the quenched reaction mixture with a water immiscible organic solvent to obtain an organic phase comprising the protected decitabine; 2) washing the organic phase with a basic aqueous solution; 3) separating the organic phase from the aqueous solution; 4) drying the organic phase to remove water; 5) and evaporating the organic solvent to obtain dry and solid protected decitabine.

9. The method of claim 6 further comprising a step of recrystallizing the β-enriched protected decitabine in an alcohol solution or an alcohol and dimethylsulfoxide (DMSO) mixture.

10. The method of claim 6 further comprising the step of drying and milling protected decitabine.

11. The method of claim 6 wherein upon completion of the deprotecting step, the β-enriched protected decitabine is isolated in solid form from undesired α-decitabine by filtration.

12. The method of claim 6 wherein the quenching step commences within 30 minutes after completion of the coupling reaction.

13. The method of claim 6 wherein the quenching step commences within 5 minutes after completion of the coupling reaction.

14. The method of claim 6 wherein the quenching step commences immediately after completion of the coupling reaction.

15. The method of claim 6 wherein the amount of primary amine is about 1 molar equivalent with respect to the 2-deoxyribofuranose of formula II.

16. The method of claim 1 wherein the coupling reaction is conducted at a temperature of −60° C. to 5° C.

17. The method of claim 16 wherein the temperature is about 0° C.

18. The method of claim 8 wherein the basic aqueous solution is sodium bicarbonate solution.

19. A method for producing a β-enriched protected decitabine of formula I:

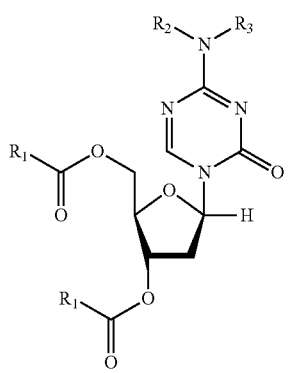

wherein each of $R_1$ is $C_1$-$C_8$ alkyl group or aryl group, each of $R_2$ and $R_3$ is independently hydrogen or $Si(R_4)_3$, and $R_4$ is independently optionally substituted $C_1$-$C_8$ alkyl group or aryl group, comprising:

a) coupling a protected 2-deoxy-ribofuranose of formula II:

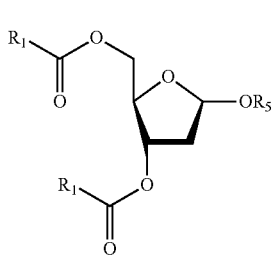

wherein each of $R_1$ is as defined above, and $R_5$ is alkylcarbonyl group, arylcarbonyl group, alkylsulfonyl group, fluoroalkylsulfonyl group or arylsulfonyl group, with a protected 5-azacytosine, of formula III:

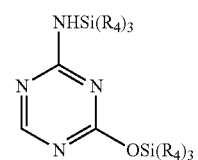

wherein each of $R_4$ is as defined above, in the presence of dichloromethane and a catalyst at a temperature of −60° C. to 5° C. to form a reaction mixture comprising the protected decitabine of formula I; and b) quenching the reaction mixture of step a) with a non-aqueous primary amine base to maintain the ratio of β-anomer to α-anomer of the protected decitabine of formula I in the reaction mixture at no less than 1.5:1.

20. The method of claim 1 wherein the ratio of β-anomer to α-anomer of the protected decitabine in the reaction mixture is 1.7:1 or greater.

21. The method of claim 6 wherein the ratio of β-anomer to α-anomer of the protected decitabine in the reaction mixture is 1.7:1 or greater.

22. The method of claim 19 wherein the ratio of β-anomer to α-anomer of the protected decitabine in the reaction mixture is 1.7:1 or greater.

* * * * *